United States Patent

Tellini

[11] Patent Number: 5,607,456
[45] Date of Patent: Mar. 4, 1997

[54] ARTIFICAL CARDIAC PACEMAKER WHICH EMITS STIMULI LOCKED TO THE ELECTRIC IMPULSION OF THE NATURAL CARDIAC PACEMAKER

[76] Inventor: Luigi Tellini, 160, Frz. Rigutino, I-52040 Arezzo, Italy

[21] Appl. No.: 318,111

[22] Filed: Oct. 5, 1994

[30] Foreign Application Priority Data

Dec. 14, 1993 [IT] Italy .................. AR93A0032

[51] Int. Cl.⁶ .................................. A61N 1/362
[52] U.S. Cl. .................................. 607/9
[58] Field of Search .................. 607/9, 14, 25, 607/30, 32

[56] References Cited

U.S. PATENT DOCUMENTS

| | | | |
|---|---|---|---|
| 4,284,082 | 8/1981 | Funke et al. | 607/9 |
| 4,920,965 | 5/1990 | Funke et al. | 607/9 |
| 4,941,471 | 7/1990 | Mehra | 607/9 |
| 5,016,630 | 5/1991 | Moberg | 607/9 |
| 5,312,447 | 5/1994 | Begemann | 607/9 |
| 5,340,361 | 8/1994 | Sholder | 607/9 |

*Primary Examiner*—William E. Kamm
*Assistant Examiner*—Kennedy J. Schaetzle
*Attorney, Agent, or Firm*—Young & Thompson

[57] ABSTRACT

The invention concerns a cardiac pacemaker consisting of electronic circuitry including a natural beat detector unit, an artificial stimuli generating unit whose escape interval is phase-locked to the natural beat, a programmed memory control unit which regulates its functioning as well as a switch unit which cuts out the artificial stimulus when the natural one reaches a condition considered normal.

15 Claims, 2 Drawing Sheets

ARTIFICAL CARDIAC PACEMAKER WHICH EMITS STIMULI LOCKED TO THE ELECTRIC IMPULSION OF THE NATURAL CARDIAC PACEMAKER

BACKGROUND OF THE INVENTION

1. Field of the Invention

The invention concerns a cardiac pacemaker which, via an electrode implanted in the atrial and/or ventricular cavity, emits effective electric pulses aimed to keep cardiac contractions regular and constant.

2. Description of the Related Art

Currently, in the field of permanent or temporary cardiac pacing, pacemakers exist, all of which are characterized by an escape interval which determines a stimulation frequency that bears no relation to the sequence of natural electric pulses at the base of the heart's natural functioning and which make up the framework in which the pacemaker has to work.

Existing electrostimulators have an escape interval that is programmed to a fixed rate, usually selected within a range that guarantees a heart rate of between 70 and 80 beats per minute. Some pacemakers, of the so-called "Rate Responsive" (R.R.) type, adjust the frequency to meet the demands of increased cardiac load during movement or effort.

In this case the increased cardiac frequency corresponds to muscular activity discerned by strain occuring in piezoelectric sensors, by sensors which measure pulmonary ventilation and by other types of sensors. Other so-called "hysteresis" pacemakers progressed from a single to two escape intervals: one, longer interval for the initial triggering of the artificial pacemaker and the other, shorter and constant interval for subsequent stimulation intervals in the case of prolonged cardiac pacing. In order to favour the maintenance of the natural rhythm even more, this method was subsequently modified with the advent of the "search hysteresis" pacemaker. In this case the deactivation threshold of the artificial pacemaker is occasionally adjusted so as to favour the re-emergence of the natural rhythm. However, even with the application of hysteresis, the escape intervals are fixed. During a check-up it is possible to set them to different rates, but once memorized, they can no longer adjust automatically to adapt to the variations in the patient's heart rate.

With the introduction of the "rate responsive" function, the escape intervals are spread over a much wider range in an attempt to adapt to increases in the patient's metabolic demands. There still remains the fact that with both the "rate responsive" and the "hysteresis" equipped pacemakers, the escape interval is completely unconnected to natural electric stimuli which very often continue to be set off and appear, even though in an irregular and inefficient way.

Existing cardiac pacemakers therefore can interfere with the natural rhythm, nullifying the daily physiological variation of the sinusal drive, destroying the physiological triggering sequence between the atrium and the ventricle and provoking a serious cardio-circulatory imbalance termed "pacemaker syndrome".

OBJECTS AND SUMMARY OF THE INVENTION

The aim of the current invention is to eliminate the disadvantages inherent in existing pacemakers and to create a device which, employing straightforward electronic circuitry that is simple to make using existing electronic technology, will effect electric cardiac stimulation that respects natural rhythm and makes necessary adjustments so as to keep alterations in the rate of natural heart beats to a minimum. With this device the escape beats are not located arbitrarily based on a preset interval, but are located either where we would expect them to be or in the most suitable place. This is, therefore, a device which works together with the natural pacemaker without disturbing its natural functioning and reintegrates missed beats into a position where they should be according to natural rhythms.

The invention that makes these results possible consists of a pacemaker made up of electronic circuitry including a natural beat detector block, an artificial stimuli generating block with escape interval locked in phase and, if necessary, in frequency to the former, a programmed memory control block which regulates its functioning as well as a switch which cuts out the artificial stimulus when the natural one reaches a condition considered normal.

The device can be developed in detail according to two types of embodiment inextricably linked to the same principle at the basis of the invention, that is the phase-locking of the artificial beat to the natural one, carried out using the escape interval.

With the first solution the invention is made with a mixed analogical/digital circuit, hereon termed "analogical", whose natural beat detector unit and locked-in artificial stimuli generatoring unit are combined with a programmed memory that carries out both the control of the frequency and the prevention or cutting-out of the artificial stimulus using a master switch when the natural stimulus has returned to normal conditions.

Control of the stimulation frequency is effected via a divider block. The output frequency of the oscillator block is in fact sent back to the phase-detector after having passed through the divider block.

With such a solution the artificial stimulator takes account of and continuously updates its memory to the control voltage of an oscillator whose frequency is in proportion to the control voltage. The escape interval is made equal to the cycle generated by the last control voltage update or by the average voltage calculated on the last two or three natural cycles.

With a second solution the invention is made with an almost entirely digital circuit based on counters and a microcontroller.

In this case the adjustment and update of the stimulation cycle to the natural cycle is obtained with the use of digital counters which work under the control of a programmed memory block that has a command and control function.

The invention in question offers important advantages both in the treatment of conduction blocks and in the treatment of bradycardia due to the fact that the proposed pacemaker is able to provide an infinite variety of escape intervals each being the most suitable in that particular clinical context.

BRIEF DESCRIPTION OF THE DRAWINGS

The design and functional logic of the invention is described in detail below with reference to two embodiments and the diagrams on the attached tables, where:

In FIG. 10, the frequency of the ventricular beats is suddenly halved, but the cardiac frequency is returned to its normal frequency by the intervention of the pacemaker. This intervention stops as soon as the block stops and the natural frequency returns to a normal rate.

It must be made clear, however, that the block diagrams and other diagrams serve only to illustrate the subject of the invention and its functional examples and are in no way intended to restrict the invention.

DESCRIPTION OF THE PREFERRED EMBODIMENTS

Figure 1:
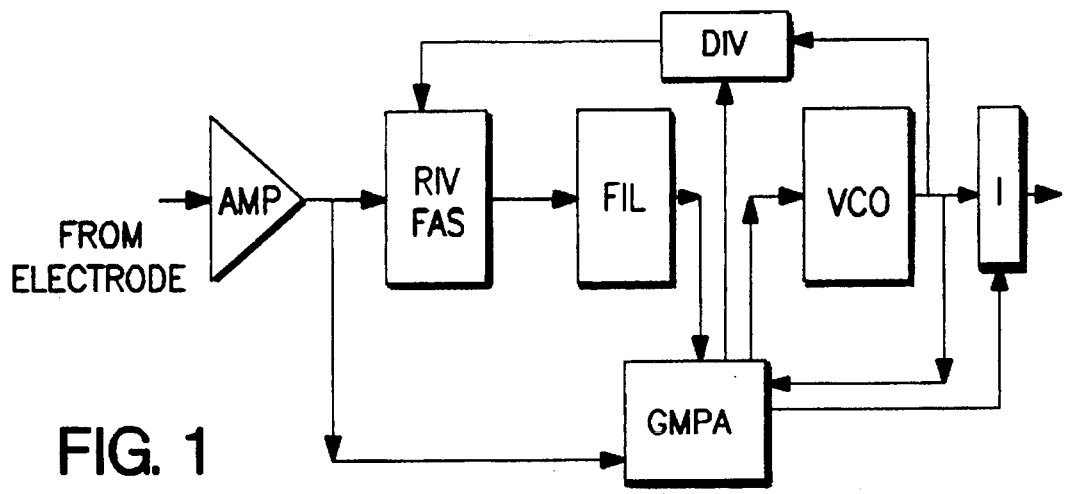
FIG. 1 is a block diagram exemplifying an embodiment of the invention realized with an "analogical"-type phase-locked-loop circuit and voltage-controlled oscillator.

In the block diagram in FIG. 1 exemplifying the analogical solution, the letters AMP stand for a block used to amplify the electric signal taken from the probe that detects natural electric pulses, which is normally inserted in the right atrium and/or ventricle. The letters RIV FAS represent a phase detecting block. FIL represents a low-pass filter used to select the right output signal from the phase detector and screen out noise and upper harmonics.

The letters VCO stand for the voltage controlled oscillator block; DIV, the divider block, whilst GMPA represents a programmed memory block that is able to memorize analogically or digitally the controlled voltage of the VCO.

I represents the switch that suppresses or turns off the signal coming from the pacemaker.

Figure 2:
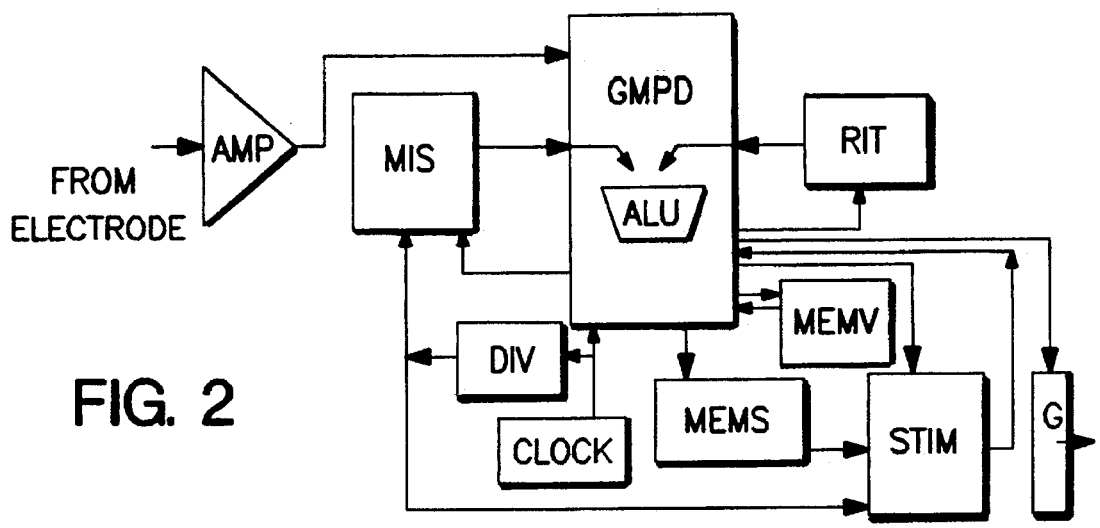
FIG. 2 is a block diagram exemplifying an embodiment of the invention making use of digital-type electronic circuitry.
Figure 10:
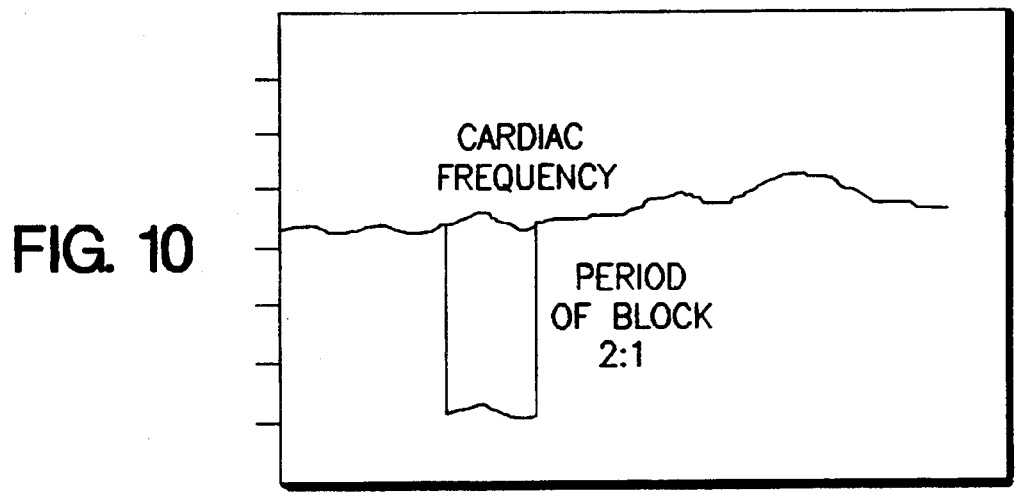
FIG. 10 exemplifies an interval during which a sudden 2:1 atrioventricular block appears which sets off the intervention of the phase-locked pacemaker.

In the block diagram in FIG. 2, exemplifying the digital solution, the letters AMP represent a block used to amplify the electric signal taken from the probe that detects natural electric pulses; GMPD represents the digital programmed memory block; CLOCK, a pulse generator; DIV, a divider block; MIS, a digital counter, MEMS, a memory; STIM a backward counter; MEMV, a memory register; RIT a memory register; ALU, a register employed to make logical and mathematical calculations; whilst the letter G represents a switch or a pulse generator that is operated by the GMPD.

When in operation, in the case of the circuit in FIG. 1, the natural signal coming from the detector probe is amplified by the AMP block and sent to the phase detector block RIV FAS, where the signal produced by the oscillator block VCO also comes in. Having compared the two signals, the RIV FAS block sends a signal which, stripped of noise signals and upper harmonics, is in proportion to the phase difference between the two, contrasted signals.

The outgoing voltage from the filter FIL therefore controls, after having passed through the GMPA block, the frequency of the VCO's outgoing signal.

Depending on this voltage, the frequency of the VCO's outgoing signal, fractionized or not by the divider block, undergoes a deviation in its central frequency until it is phase-locked to the natural incoming signal.

The programmed memory GMPA updates its memory to the value of the FIL block's outgoing voltage.

This voltage controls the VCO block's oscillation period and therefore its stimulation period. The GMPA block, on the basis of the instructions and the signals received from the AMP and VCO blocks, adjusts the divider block DIV so that the frequency of the VCO block's outgoing signal has a value that is most suitably compared with the natural signal. The VCO's outgoing signal is locked in phase to the natural cycle and has a frequency ratio that is programmed and effected using the divider DIV.

The GMPA block also controls the intervention of the switch I. In fact, every time a natural beat is detected before the pulse is emitted by the VCO, the stimulus to the heart is suppressed.

In the case of the digital circuit exemplified in the block-diagram in FIG. 2, the natural electric signal is amplified and "conditioned" by the AMP block, then sent to the memory block GMPD and measured by the digital counter MIS which is driven, together with the STIM counter, by the pulse generator CLOCK via the divider block DIV which reduces the frequency.

The pulse signal produced by the CLOCK generator is also sent to the programmed memory block GMPD.

The DIV block's outgoing signal must have a much shorter period than that of a normal beat.

The length of the natural beat is considered on the basis of the number of CLOCK pulses counted between two consecutive natural electric pulses.

Therefore precision considered as temporal resolution is inversely related to the length of the CLOCK's cycle.

The count accumulated on the counter register MIS is immediately read and assessed by the control block GMPD comparing it with the count previously stored in the memory block MEMV. The count can also be manipulated (for example divided by a suitable factor in the case of a block in the heart's conduction or in the case of "overdrive" stimulation) in the appropriate ALU register, used to make logical and mathematical calculations.

If considered suitable, the count or its derived value is recorded in the MEMV and MEMS memories. In the case of the programmed memory block GMPD deciding, depending on its commanding program, to add a positive or negative time lapse to the time measured by the MIS counter, it can extract that delay from the RIT register where it is memorized, add it to the accumulated figure in the MIS and transfer the result of the sum of the two values given on the ALU register into the MEMS memory. The memorized value on the RIT register could be altered by telemetry on the installed pacemaker; it could be definitively set; or it could be automatically altered by the GMPD block as scheduled by its commanding program. The value of the count placed in the MEMS memory is read by the STIM block which is employed to give the escape interval. The STIM is a counter which counts down from the count value taken from the MEMS memory and, once it has reached zero, makes the GMPD emit a stimulus or electric pulse. The escape interval will be equal to the period measured by the MIS block with the eventual addition of the delay or advance in time recorded on the RIT. The GMPD block, as well as its functions of valuing and manipulating the count has a controlling function on the effective emission of the stimulus or electric pulse on the heart setting off the G block which has the function of an on/off switch or a pulse generator.

Another important function of the GMPD block is that of synchronizing the signals with the natural beat. As the escape interval is synchronized with the natural beat and is the same length as the natural cycle (or a half or a third of it), the result is that the artificial stimulus is locked in phase to the natural stimulus. The phase comparison and update are carried out digitally.

The invention in question, regardless of the fact that either the circuit in FIG. 1 or in FIG. 2 is used, makes the escape interval of the artificial stimulator equal to the period of the natural pacemaker or in rational proportion to it, guaranteeing, apart from the phase-locking of the signals, constant frequency ratios between the two oscillators.

Figure 6:
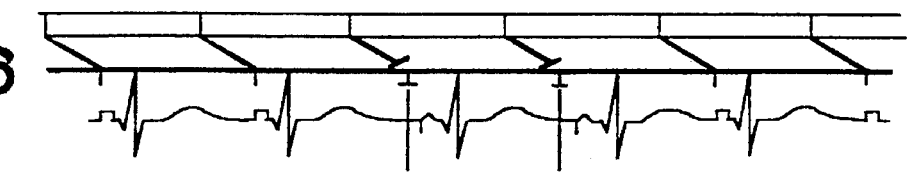
FIG. 6 exemplifies AAI-type stimulation where two instances of sinoatrial block are shown.
Figure 7:
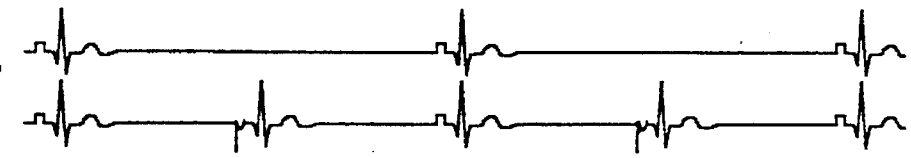
FIG. 7 and FIG. 8 exemplify a sinusal bradycardia stimulated in overdrive where the pacemaker (with atrial stimulation and sensing in FIG. 7 and with ventricular stimulation and sensing in FIG. 8 has a stimulation period that is half the natural one and is locked in phase to it without the artificial pulses interfering with the natural ones.
Figure 8:
Figure 9:
FIG. 9 also exemplifies a sinusal bradycardia stimulated in "overdrive" where the frequency of the pacemaker is such that for every two periods of natural stimulus there are three periods of artificial stimulus with the suppression of one natural stimulus.

Therefore, at times the escape interval could be exactly the same (with a minimum of programmable variations either way) as the period of the natural pacemaker, (see examples reproduced in FIGS. 3, 4, 5 and 6), or, at times it could be half of this, as exemplified in FIGS. 7 and 8 so as to double the cardiac frequency. Other times it could have a value that means that three pacemaker periods are equal to two natural periods as exemplified in FIG. 9. Other ratios between the natural oscillator and artificial one could also be chosen. The important fact is that these ratios remain constant over time due to the phase-locking.

If, for some time, there were no more natural electric signals available to update the escape interval, the pacemaker could be programmed to take a pre-arranged course of action: in the simplest case, for example, it could keep the voltage or count value resulting from the last phase comparison in its memory and continue to emit electric pulses in synchronicity with the memorized period: in a more complicated case for example, but with more effective results, after a substantially prolonged period of absence of natural reference signals, the pacemaker could follow the emission of the stimulus, according to the memorized cycle, with a slow scanning towards lower stimulating frequencies, searching for natural electric signals.

In many cases it seems favourable to place the artificially stimulated beat with a slight delay with regard to the predicted time of the natural beat, as exemplified in FIGS. 3, 4, 5 and 6, in the case of an elongation of the sinusal cycle.

The invention has the particular advantage, as it is controlled by a functional logic, of guaranteeing non-interference with the natural pacemaker and, furthermore, it favors the maintenance of synchronicity between the natural and the artificial pacemaker, in the place where they can alternate with the electric stimulation of the heart. In the case of a sudden block of the natural electric pulse or the failure to detect the same, the patient is not subjected to a sudden variation in cardiac frequency. The transition from natural to artificial stimulation (which, in this way, is integrative and not substitutive) is smooth and could even go unnoticed by the patient.

The artificial pacemaker is linked in phase, and, if necessary, in frequency, to the natural pacemaker by the escape interval, which is continuously updated and any variation in the natural pacemaker's frequency would lead to a parallel variation in the frequency of the artificial stimulator: in this way an additional "rate responsive" function is obtained based on the natural pacemaker's response to increases in work load or stimuli from the nervous system or catecholamine.

With this invention it is possible to effect an "overdrive" type of stimulation with the artificial pacemaker having stimulation intervals that are whole submultiples of the natural pacemaker's stimulation interval or are normally in a whole number ratio to this. This guarantees a proper stimulation frequency in the case of bradycardia without strongly interfering with the natural pacemaker, given that the artificial stimulus is always in phase with the natural one. In this way, not only is the sequence of natural beats undisturbed (or minimally disturbed), but the natural increase in cardiac frequency, usually limited in these cases, can be amplified according to a programmable multiplication factor. Thus, for example, a sinusal bradycardia of 37 beats per minute can create a ventricular stimulation interval corresponding to a frequency of 74 beats (overdrive with doubling) half of which are generated by the natural pacemaker and half by the artificial one (FIG. 7 and FIG. 8). Furthermore, if the natural frequency goes up, even a little, reaching, for example 45 beats a minute, the cardiac frequency duly rises to 90 beats a minute. In this case a variation in the natural beat of 8 beats a minute provokes an increase in cardiac frequency of 16 beats.

Figure 3:
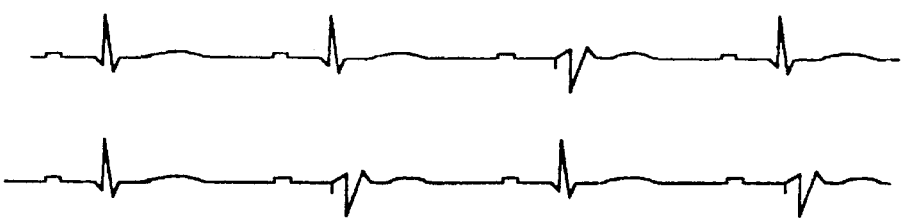
FIG. 3 exemplifies heart stimulation with phase and frequency locked to the natural cycle, carried out using ventricular stimulation and sensing. The top line shows a sporadic atrioventricular block, whilst the bottom line represents an alternating atrioventricular block.

In the case of an intermittent sinoatrial or atrioventricular block, the invention can guarantee the correct positioning of the atrial contraction (FIGS. 5 and 6) and the ventricular contraction (FIG. 3). In the case of an intermittent atrioventricular block, even a simple monocameral stimulation VVI (FIG. 3) can maintain the right sequence between atrial and ventricular pulse: the pacemaker "guesses" the correct positioning of the artificial stimulus because it has memorized "the place where it should go".

Figure 4:
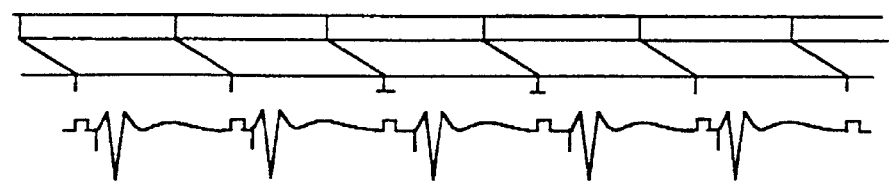
FIG. 4 represents an example of VDD stimulation in which the signal set up by the depolarization of the atrium is not picked up correctly, but the artificial stimulation produces ventricular stimulation suitable to the context inspite of this problem.
Figure 5:
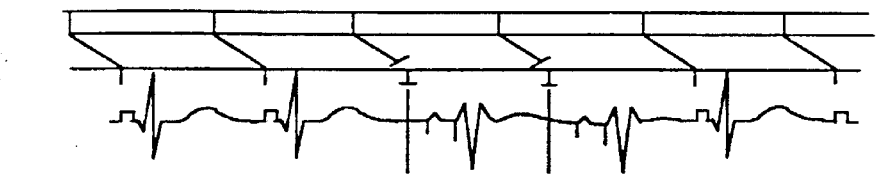
FIG. 5 exemplifies DDD stimulation with phase and frequency locked to the sinusal drive where two consecutive instances of sinoatrial block are shown.

According to the same principle, the type of operation suggested is also useful in different stimulation modes such as VDD, DDD and AAI (see FIGS. 4, 5 and 6).

With more complex stimulation modes such as VDD and DDD, there is already a phase locking with the natural stimulus by the ventricular depolarization produced by the artificial pacemaker. The locking is effected via the emission of a pulse synchronized with the natural beat. The fact that these systems work well however, is critically dependent on the picking up of natural reference signals.

When natural reference signals are not picked up, either because they are absent or because they are too weak, even this type of pacemaker undergoes a "crisis" and emits the stimulus after an arbitrary escape interval.

This occurs because it has not memorized the natural cycle and it has not been able to base the escape interval on this cycle.

The invention facilitates the recognition of extrasystoles. Any sudden variation in the natural cycle, with a significant deviation from the memorized value that is not in exact ratio with the cycle stored in its memory, would be considered a premature beat. Depending on each case, the pacemaker could be programmed to ignore a premature beat, in order to update the escape interval, thus maintaining the correct phase ratio with the sinusal pacemaker.

The memorization of the length of the natural cycle can also be used for the function of "windowing", that is to completely ignore weak electric signals due to noise occurring in a period that is noticeably different from that in which the natural cardiac signal would be expected to occur. This function could be useful in VDD stimulation effected by a single electro-catheter with floating atrial electrode that therefore requires high amplification of the atrial signal. Knowing at which moment the atrial wave is due, one could mask the "sensing" for almost the entire cycle activating the sensors and the amplifiers only during the narrow time interval when the atrial wave is due.

The invention therefore offers a type of stimulation that, although it slightly complicates the design of a pacemaker, is to be considered a notable step forward in respect to the current state of the art. In any case, the program controlling the operation of the pacemaker includes the basic safety devices necessary to switch off the locking function in the case of it leading to a stimulation frequency that was too low or too high. The cutting out of the phase-locking would lead to the adoption of existing, more straight forward means of stimulation. In cases of overdrive stimulation for patients with bradycardia, for example, when cardiac frequency exceeds a particular threshold, the multiplication ratio would be brought down automatically (for example form 2 to 1.5).

The new way of regulating the escape interval of cardiac pacemakers is to be considered a remarkable step forward in the operation of these devices. Artificial cardiac stimulation has progressed from being substitutive to integrative. The latter term is to be understood as a form of stimulation that knows perfectly how to become an integral part of natural rhythm without making significant changes to it.

Stimulation which, due to an infinite number of possible escape intervals, can be naturally inserted in the context of the sinusal drive.

The basic novelty lies in the fact that the escape interval is no longer an arbitrary parameter, that is "dumb" and set in one place, rather it has become a dynamic, "intelligent parameter" capable of adapting to the clinical context.

I claim:

1. An artificial cardiac pacemaker which emits artificial stimuli to maintain regular and constant cardiac contractions, comprising:

electrode means, implanted in at least one of an atrial and ventricular cavity, for detecting a reference natural stimuli;

programmable control means for regulating a functioning of said pacemaker;

artificial stimuli generating means, connected to and controlled by said programmable control means, for generating said artificial stimuli;

phase detecting means, connected to said programmable control means, for detecting a phase difference between said detected reference natural stimuli and said generated artificial stimuli, an escape interval of said artificial stimuli generating means being phase-locked to the reference natural stimuli and proportional to a selected ratio between the period of the reference natural stimuli and said escape interval;

switch means, connected to said artificial stimuli generating means, for inhibiting said artificial stimuli when said natural stimuli reaches a condition considered to be normal.

2. An artificial cardiac pacemaker as claimed in claim 1, wherein said escape interval of the artificial stimuli generator is either equal to a period of the reference natural stimuli or locked to said period of said reference natural stimuli according to rational proportions which guarantee constant frequency ratios between the escape interval and said period of said reference natural stimuli.

3. An artificial cardiac pacemaker as claimed in claim 2, wherein said programmable control means further comprises memory means for storing and continuously updating the period of said reference natural stimuli.

4. An artificial cardiac pacemaker as claimed in claim 3, wherein said control means, if said reference natural stimuli are not detected by said electrode means, controls said artificial stimuli generating means to either generate said artificial stimuli with a period equal to said stored period of said reference natural stimuli, or to begin a scanning toward lower stimulating frequencies to search for said reference natural stimuli.

5. An artificial cardiac pacemaker as claimed in claim 1, wherein, when necessary, said control means controls said artificial stimuli generating means to generate said artificial stimuli with either a slightly positive or a slightly negative time lapse relative to the period of the reference natural stimuli.

6. An artificial cardiac pacemaker as claimed in claim 3, wherein said control means is programmed to ignore any sudden variation in the period of the reference natural stimuli relative to the stored value of the period of the reference natural stimuli, so as to update the escape interval.

7. An artificial cardiac pacemaker as claimed in claim 1, wherein said control means is programmed so as to ignore weak signals due to noise that occur in a time period that is substantially different from the time period in which the reference natural stimuli is predicted to occur.

8. An artificial cardiac pacemaker as claimed in claim 2, wherein said control means switches off said locking of said escape interval to said period of said reference natural stimuli when said generated artificial stimuli has a cardiac stimulation frequency that is either too low or too high.

9. An artificial cardiac pacemaker as claimed in claim 1, made with an analog electronic circuit, further comprising:

filter means, having an input connected to an output of said phase detector means and an output connected to said programmable control means, for low-pass filtering an output of said phase detector means;

a voltage controlled oscillator means, connected to said control means, an oscillation period of said voltage controlled-oscillator depending on a value stored in said control means corresponding to said output of said filter means, said control means comprising memory means for storing at least said value;

a dividing means, connected to and controlled by said control means, for dividing an output of said voltage controlled oscillator and for feeding a dividing means output signal to said phase detecting means, to thereby insure that a frequency of said generated artificial stimuli is either equal to the frequency of the reference natural stimuli or proportional to a selected ratio between the frequency of the artificial stimuli and the frequency of the reference natural stimuli.

10. An artificial cardiac pacemaker as claimed in claim 9, wherein in the presence of bradycardia, the dividing means is driven by the programmable control means to divide according to a programmed division factor.

11. An artificial cardiac pacemaker as claimed in claim 9, wherein said programmable control means automatically reduces a multiplication ratio in the dividing means when the cardiac frequency exceeds a certain threshold.

12. An artificial cardiac pacemaker as claimed in claim 1, made with a digital electronic circuit, further comprising at least one digital counter means, connected to said programmable control means, for regulating and updating said artificial stimuli to either correspond to said reference natural stimuli, or to be proportional to a selected ratio between the period of the artificial stimuli and the period of the reference natural stimuli, said at least one digital counter means being controlled by a program controlling said programmable control means.

13. An artificial cardiac pacemaker as claimed in claim 1, made with a digital electronic circuit, further comprising a pulse generator means and at least one digital counter means, said pulse generator means, through said programmable control means connected thereto, driving said at least one digital counter means to measure said reference natural stimuli after said reference natural stimuli has been detected by said electrode means.

14. An artificial cardiac pacemaker as claimed in claim 13, made with an electronic digital circuit, wherein a frequency of pulses generated by said pulse generator means has a greater frequency then the frequency of the reference natural stimuli.

15. An artificial cardiac pacemaker as claimed in claim 1, made with an electronic digital circuit, further comprising register means, connected to said programmable control means, for storing either a positive or negative time lapse to be added to the period of the natural stimuli, said positive or negative time lapse being either fixed, automatically adjusted by said program controlling said controlling means, or adjusted by telemetry through telemetry means.

* * * * *